Figure 1:
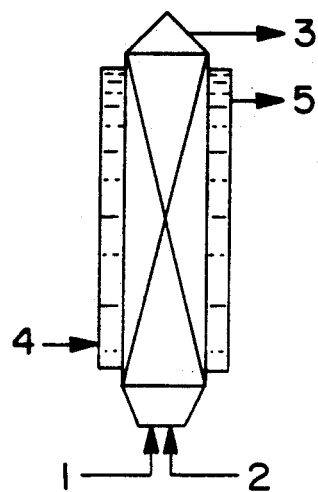

United States Patent [19]

Ichihana et al.

[11] Patent Number: 5,248,754
[45] Date of Patent: Sep. 28, 1993

[54] PROCESS FOR CONTINUOUS PRODUCTION OF POLYCARBONATE OLIGOMER

[75] Inventors: Hideyuki Ichihana, Yokohama; Noboru Yamanishi; Koji Hashimoto, both of Matsuyama, Japan

[73] Assignee: Teijin Chemicals, Ltd., Tokyo, Japan

[21] Appl. No.: 913,421

[22] Filed: Jul. 15, 1992

[30] Foreign Application Priority Data

Jul. 19, 1991 [JP] Japan .................. 3-203556

[51] Int. Cl.$^5$ ............................................. C08G 64/24
[52] U.S. Cl. .................................... 528/196; 528/202
[58] Field of Search ................................ 528/196, 202

[56] References Cited

U.S. PATENT DOCUMENTS

| | | | |
|---|---|---|---|
| 4,089,888 | 5/1978 | Tokumitsu et al. | 260/463 |
| 4,122,112 | 10/1978 | Koda et al. | 260/463 |
| 4,601,858 | 7/1986 | Shannon et al. | 558/281 |
| 4,767,840 | 8/1988 | Shannon et al. | 528/196 |

FOREIGN PATENT DOCUMENTS

| | | |
|---|---|---|
| 2092 | 1/1971 | Japan . |
| 21460 | 6/1971 | Japan . |
| 44091 | 10/1981 | Japan . |
| 108225 | 6/1983 | Japan . |

*Primary Examiner*—Harold D. Anderson
*Attorney, Agent, or Firm*—Sherman and Shalloway

[57] ABSTRACT

The present invention provides a process for producing a polycarbonate oligomer continuously, which comprises feeding (a) an aqueous alkali solution of a dihydric phenol and (b) phosgene into a tower type reactor from the bottom to react them in the reactor without using any organic solvent and discharging the reaction mixture from the top of the reactor. According to this process, an oligomer giving a polycarbonate of stable quality can be produced using a simple apparatus.

6 Claims, 1 Drawing Sheet

PROCESS FOR CONTINUOUS PRODUCTION OF POLYCARBONATE OLIGOMER

The present invention relates to a process for producing a polycarbonate oligomer by reacting an aqueous alkali solution of a dihydric phenol with phosgene. More particularly, the present invention relates to a process for continuously producing an oligomer giving a polycarbonate of stable quality, using a simple apparatus.

There are known processes for producing a polycarbonate oligomer continuously by reacting an aqueous alkali solution of a dihydric phenol with phosgene in the presence of an organic solvent. In these processes, however, the heat of reaction generated must be removed in order to suppress the decomposition of phosgene or formed chloroformate or the boiling of the organic solvent, which made complex the apparatus used. In, for example, the process disclosed in Japanese Patent Publication No. 21460/1971 or No. 44091/1981 wherein gas-phase phosgene is contacted with an aqueous alkali solution of a dihydric phenol and an organic solvent both of atomized state and the heat of reaction generated is absorbed by the heat of vaporization of the organic solvent, a long reaction pipe must be used in order to recondensate the vaporized organic solvent. In order to solve this inconvenience, there was proposed a process using a tower type reactor fitted with a cooling jacket, in Japanese Patent Application Kokai (Laid-Open) No. 108225/1983 or No. 108226/1983. In this process, however, it is necessary to use a pipe of small diameter for efficient cooling, but the use makes difficult the smooth reaction between droplets and gas in the reactor. It is also known to react an aqueous alkali solution of a dihydric phenol with phosgene without using any organic solvent. For example, Japanese Patent Publication No. 2092/1971 discloses a process which comprises adding phosgene to an aqueous solution of an aromatic diol to produce a diol monochloroformate, and Japanese Patent Application Kokai (Laid-Open) No. 26251/1987 discloses a process which comprises blowing phosgene into a solution containing a di(alkali metal) salt of an organic dihydroxy compound, with stirring to produce a bis-chloroformate composition. These prior arts, however, make no mention of continuous production of polycarbonate oligomer.

The object of the present invention is to produce a polycarbonate oligomer having a relatively low molecular weight and constant properties, continuously and efficiently by reacting an aqueous alkali solution of a dihydric phenol with phosgene using a simple apparatus wherein the storage of a large amount of phosgene is unnecessary.

The present inventor made study to achieve the above object. As a result, it was found that a continuous process using a tower type reactor but using no organic solvent can suppress heat generation by reaction, can keep the decomposition of phosgene and chloroformate at low levels, and gives an oligomer of relatively low molecular weight and that the polymerization of said oligomer can give a polycarbonate of stable quality. It was also found that while in the conventional processes using no organic solvent, the formed oligomer is precipitated in the aqueous phase, which tends to cause residence and blocking and makes difficult continuous production, this problem can be solved by feeding (a) an aqueous alkali solution containing a particular concentration of a dihydric phenol and (b) phosgene, at a particular ratio into a tower type reactor from the bottom and discharging an aqueous slurry containing a reaction product, from the top of the reactor.

According to the present invention, there is provided a process for producing a polycarbonate oligomer continuously, which comprises continuously feeding (a) an aqueous alkali solution containing 100-230 g/liter of a dihydric phenol and (b) 1.0-1.3 moles, per mole of said dihydric phenol, of phosgene into a tower type reactor from the bottom to react them in the reactor without using any organic solvent and discharging the resulting polycarbonate oligomer from the top of the reactor.

As the dihydric phenol used in the present invention, bisphenols are preferred. 2,2-bis-(4-hydroxyphenyl)propane (hereinafter referred to as bisphenol A) is particularly preferred. Other bisphenols include, for example, bis(4-hydroxyphenyl)methane, 1,1-bis(4-hydroxyphenyl)ethane, 2,2-bis(4-hydroxyphenyl)-butane, 2,2-bis(4-hydroxyphenyl)pentane, 2,2-bis-(4-hydroxyphenyl)hexane, 2,2-bis(4-hydroxyphenyl)-4-methylpentane, 1,1-bis(4-hydroxyphenyl)-1-phenylethane, 1,1-bis(4-hydroxyphenyl)cyclohexane, 2,2-bis(4-hydroxy-3-methylphenyl)propane, 2,2-bis(4-hydroxyphenyl)-hexafluoropropane, and 2,2-bis(3,5-dibromo-4-hydroxyphenyl)propane.

The dihydric phenol is used by dissolving it in an aqueous alkali solution. The alkali is preferably an alkali metal hydroxide such as sodium hydroxide, potassium hydroxide or the like. The concentration of the alkali metal hydroxide in the aqueous solution is preferably 5-10% by weight. The molar ratio of the dihydric phenol and the alkali is preferably 1:1.9 to 1:3.2, more preferably 1:2.0 to 1:2.5. The concentration of the dihydric phenol in the aqueous alkali solution is as high as possible in view of the productivity of the present process, but is preferably 100-230 g/liter in view of the solubility of the dihydric phenol and the transportation of the product slurry obtained. The preparation of the aqueous alkali solution of a dihydric phenol must be conducted at a temperature of 20° C. or above. In the preparation, however, in order to prevent the dihydric phenol from being oxidized, it is preferable to conduct the dissolution operation at a temperature as low as possible and in a nitrogen atmosphere, or to add a small amount of a reducing agent such as hydrosulfite or the like.

Phosgene is used in a liquid state or a gaseous state. The use in a gaseous state is preferable. This phosgene may contain a halogenated hydrocarbon such as carbon tetrachloride. When carbon tetrachloride-containing phosgene is used in a conventional process using an organic solvent, there arises a problem that the carbon tetrachloride contained in phosgene is captured by a polymer when the formed polycarbonate oligomer is polymerized into said polymer; in the present invention, however, there occurs no such problem. The preferable amount of phosgene used differs by the reaction conditions (in particular, the temperature of tower type reactor and the concentration of dihydric phenol in aqueous alkali solution) but, under the conditions employed in the present invention, the amount of phosgene used is sufficiently 1.0-1.3 moles, preferably 1.05-1.25 moles per mole of the dihydric phenol. The residence time in tower type reactor, i.e. the reaction time between dihydric phenol and phosgene is preferably 1-300 seconds, more preferably 3-100 seconds. When the residence time is less than 1 second, the reaction is insufficient. When the residence time is more than 300 seconds, the hydrolysis of chloroformate precedes the intended reaction. The residence time in the reactor is adjusted depending upon the effective volume of the reactor and the flow rates of the raw materials fed into the reactor.

Figure 2:
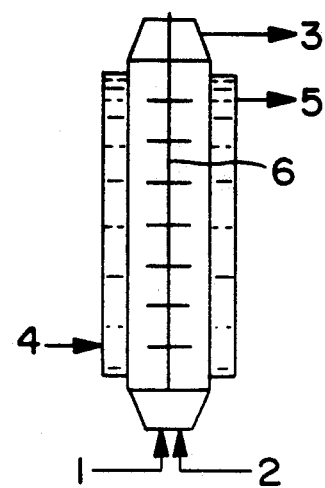
Figure 3:
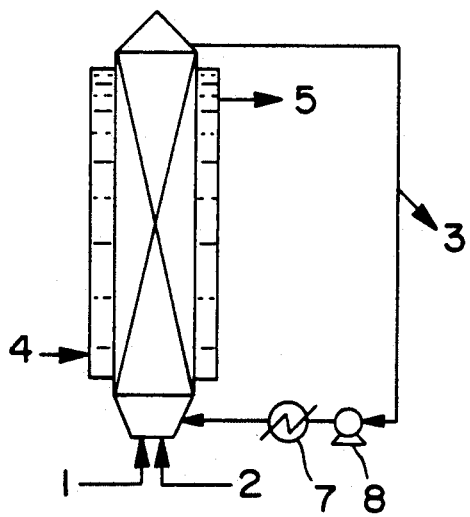
Figure 4:
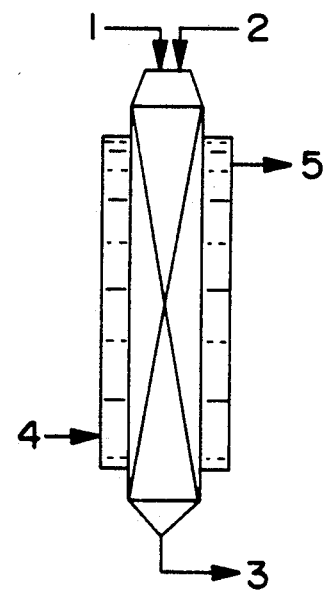

In the accompanying drawings,

FIG. 1, FIG. 2 and FIG. 3 are schematic views showing three different tower type reactors each suitable for carrying out the present invention; and FIG. 4 is a schematic view showing an apparatus used in Comparative Example 3 described later.

In FIGS. 1 to 4, 1 is an inlet for phosgene; 2 is an inlet for an aqueous alkali solution of a dihydric phenol; 3 is an outlet for a reaction mixture; 4 is an inlet for cooling water; and 5 is an outlet for cooling water.

FIG. 1 shows a case wherein the inside of tower type reactor is empty. FIG. 2 shows a case wherein an agitating element 6 is accomodated inside the tower type reactor. FIG. 3 shows a case wherein part of the reaction mixture discharged from the top of tower type reactor is bypassed through a liquid-transferring pump 8 and a heat exchanger 7 and returned to the bottom of reactor. In each of these cases, an aqueous alkali solution of a dihydric phenol and phosgene are fed from the bottom of the tower type reactor, and the reaction mixture containing a formed polycarbonate oligomer is discharged from the top of the reactor. The tower type reactor preferably has a cylindrical form having an inside diameter:length ratio of 1:3 to 1:50. Since the reaction is exothermic, use of an appropriate cooling means is desirable for temperature control when the reaction is conducted on a large scale. Examples of the cooling means include a jacket enabling the passing of cooling water, the temperature control for raw materials fed, and the recirculation of part of reaction product through heat exchanger. The reaction temperature is not particularly restricted but is preferably 10°-80° C.

The preferable embodiment of the present process is described below on a case using the apparatus of FIG. 1. From the bottom of the reactor are fed phosgene through a pipe 1 and an aqueous alkali solution of a dihydric phenol through a pipe 2. A slurry reaction mixture containing a polycarbonate oligomer formed in the reactor is discharged outside from the reactor top through an outlet 3. The temperature control is not always necessary but, in the apparatus of FIG. 1, it is possible by feeding a temperature-controlled water through an inlet 4 and discharging it through an outlet 5.

The polycarbonate oligomer mixture obtained by the present process gives a polycarbonate of high molecular weight, with good reproducibility, by adding, to the mixture, an organic solvent capable of dissolving the mixture, a monohydric phenol, an amine, an alkali, etc. and subjecting the resulting mixture to a polycondensation reaction.

The present invention is described in more detail by way of Examples. In the Examples, measurements of properties were made as follows.

Relative Viscosity

Methylene chloride was added to the reaction mixture discharged from the top of reactor, and they were mixed sufficiently. Then, the resulting mixture was allowed to stand to separate into an organic phase and an aqueous phase. To the organic phase was added pure water of about the same amount, and they were mixed sufficiently. The mixture was filtered through a filter paper and then allowed to stand to separate into an organic phase and an aqueous phase. This water washing for organic phase was repeated until no chlorine ion was detected in the separated aqueous phase by silver nitrate. The solvent was removed from the organic phase by vaporization, and the residue was dried under vacuum. 0.700 g of the thus obtained oligomer or polymer was dissolved in 100 ml of methylene chloride and measured for relative viscosity at 20° C. using an Ostwald viscometer.

Concentration of Bisphenol A in Aqueous Phase

Part of the aqueous phase separated in the first phase separation in the above procedure for measurement of relative viscosity, was diluted with an aqueous dilute alkali solution and measured absorbances at wavelengths of 294 nm and 330 nm using an UV spectrometer (Model 200-10 manufactured by Hitachi, Ltd.). Then, concentration of bisphenol A was determined using the following formula:

bisphenol A concentration
$$(g/liter) = (A_1 - A_0) \times n \times 1/22$$

wherein $A_1$ and $A_0$ are absorbances at 294 nm and 330 nm, respectively, and n is a degree of dilution.

Concentration of Sodium Carbonate in Aqueous Phase

For the remainder of the aqueous phase used in the above determination of bisphenol A concentration, concentration of sodium carbonate (g/liter) was determined by the Winkler method.

Molecular Weight Distribution

The polymer obtained in the measurement of relative viscosity was dissolved in tetrahydrofuran to prepare a tetrahydrofuran solution containing 1% by weight of the polymer. The solution was subjected to gel permeation chromatography using ALC/GPC 201 manufactured by Waters, whereby the Mw/Mn of the polymer which is a ratio of the weight-average molecular weight (Mw) and the number-average molecular weight (Mn), was determined. A Mw/Mn closer to 1 indicates a narrower molecular weight distribution.

EXAMPLE 1

An apparatus of FIG. 1 was used. The tower type reactor was a cylindrical pipe with a glass lining, having a length of 650 mm and an inside diameter of 160 mm. Bisphenol A was dissolved in an aqueous solution containing 7.0% by weight of sodium hydroxide, at 30° C. to prepare an aqueous sodium hydroxide solution containing 165 g/liter of bisphenol A (specific gravity = 1.08).

Phosgene (purity = 98% by volume, contains 2% by volume of CO) was fed into the tower type reactor through an inlet 1 at a rate of 14.5 kg/hr, and simultaneously the above-prepared aqueous sodium hydroxide solution of bisphenol A was fed through an inlet 2 at a rate of 199 kg/hr. A temperature-controlled cooling water was fed through an inlet 4, whereby the temperature inside the reactor become 40±1° C. The reaction mixture discharged from an outlet 3 was sampled 10 times at intervals of 30 minutes starting from 1 hour after the beginning of the discharging, and analyzed according to the methods described above. As a result, the relative viscosity of oligomer was 1.035–1.038; the concentration of bisphenol A in aqueous phase was 45–47 g/liter; the concentration of sodium carbonate in aqueous phase was 5.2–5.8 g/liter; thus, all the data were very stable.

Next, 1.5 liters of the portion of the reaction mixture which was not sampled, together with 750 ml of methylene chloride, 55 g of an aqueous solution containing 30% by weight of sodium hydroxide, 3.2 g of tert-butylphenol and 0.15 g of triethylamine, was fed into a 2-liter flask fitted with a stirrer. The mixture was subjected to a reaction at 25° C. for 2 hours. The resulting polycarbonate had a relative viscosity of 1.429 and a Mw/Mn of 2.46.

EXAMPLE 2

The same procedure as in Example 1 was used except that no cooling water was used and resultantly the temperature inside the reactor became 70±° C. The reaction mixture discharged from the outlet 3 was sampled 10 times at intervals of 30 minutes starting from 1 hour after the beginning of the discharging, and analyzed according to the method described above. As a result, the relative viscosity of oligomer was 1.037–1.045; the concentration of bisphenol A in aqueous phase was 42–44 g/liter; the concentration of sodium carbonate in aqueous phase was 5.3–5.9 g/liter; thus, all the data were very stable. The polycarbonate obtained by the polymerization of the oligomer had a relative viscosity of 1.424 and a Mw/Mn of 2.56.

COMPARATIVE EXAMPLE 1

The same procedure as in Example 1 was used except that phosgene was fed through the inlet 1 at a rate of 111 kg/hr in the form of a solution obtained by dissolving 170 g/liter of phosgene in methylene chloride of −15° C. The molar ratio of phosgene to dihydric phenol was the same as in Example 1 and was 1.10. The reaction mixture discharged from the outlet 3 was sampled 10 times at intervals of 30 minutes starting from 1 hour after the beginning of the discharging, and analyzed according to the methods described above. As a result, the relative viscosity of oligomer was 1.075–1.180; the concentration of bisphenol A in aqueous phase was 12–48 g/liter; the concentration of sodium carbonate in aqueous phase was 9.9–15.3 g/liter; thus, all the data were very unstable. The polycarbonate obtained by the polymerization of the oligomer had a relative viscosity of 1.260 and a Mw/Mn of 3.40.

COMPARATIVE EXAMPLE 2

The same procedure as in Example 1 was used except that phosgene was fed at a rate of 18.5 kg/hr. The reaction mixture became a sticky slurry and blocked the outlet 3, making impossible the continuous production of polycarbonate oligomer.

COMPARATIVE EXAMPLE 3

An apparatus of FIG. 4 was used. The tower type reactor was a cylindrical pipe with a glass lining, having a length of 1,300 mm and an inside diameter of 160 mm. Bisphenol A was dissolved in an aqueous solution containing 7.0% by weight of sodium hydroxide, at 30° C. to prepare an aqueous sodium hydroxide solution containing 165 g/liter of bisphenol A (specific gravity=1.08).

Phosgene was fed into the tower type reactor through an inlet 1 at the reactor top at a rate of 14.5 kg/hr, and simultaneously the above-prepared aqueous sodium hydroxide solution of bisphenol A was fed through an inlet 2 at a rate of 199 kg/hr. A slurry precipitated at the bottom of the reactor and blocked an outlet 3, making impossible the continuous production of polycarbonate oligomer.

As shown in the above Examples, the present invention makes it possible to produce a polycarbonate oligomer of relatively low molecular weight easily with good reproducibility, by reacting an aqueous alkali solution of a dihydric phenol with phosgene in a tower type reactor in an aqueous phase without using any organic solvent and further by feeding the raw materials from the bottom of the reactor and discharging the reaction mixture from the top of the reactor. This oligomer can be easily made into a polymer (polycarbonate) by a polycondensation reaction.

What is claimed is:

1. A process for producing a polycarbonate oligomer, which comprises continuously feeding (a) an aqueous alkali solution containing 100–230 g/liter of a dihydric phenol and (b) 1.0–1.3 moles, per mole of said dihydric phenol, of phosgene into a tower reactor from the bottom of the reactor and reacting in the absence of organic solvent and discharging the resulting polycarbonate oligomer from the top of the reactor.

2. The process according to claim 1, wherein 1.05–1.25 moles, per mole of a dihydric phenol, of phosgene is fed.

3. The process according to claim 1, wherein residence time in the reactor is 1–300 seconds.

4. The process according to claim 1, wherein reaction temperature is 10°–80° C.

5. The process according to claim 1, wherein the reactor is cylindrical and has an inside diameter:length ratio of 1:3 to 1:50.

6. The process according to claim 1 wherein the dihydric phenol is 2,2-bis-(4-hydroxyphenyl)-propane.

* * * * *